United States Patent
Torgerson et al.

(10) Patent No.: US 6,456,883 B1
(45) Date of Patent: Sep. 24, 2002

(54) APPARATUS AND METHOD FOR ALLOWING IMMEDIATE RETRIEVAL FOR INFORMATION AND IDENTIFICATION FROM AN IMPLANTABLE MEDICAL DEVICE HAVING A DEPLETED POWER SOURCE

(75) Inventors: Nathan A. Torgerson, Andover; John J. Grevious, Minneapolis; Steven L. Jensen, Andover; John W. Forsberg, St. Paul, all of MN (US); Robert Leinders, Limbricht (NL); Raymond F. McMullen, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/558,664

(22) Filed: Apr. 26, 2000

(51) Int. Cl.[7] .............................................. A61N 1/378
(52) U.S. Cl. ............................ 607/34; 607/32; 607/33; 607/60
(58) Field of Search ............................ 607/4, 5, 9, 33, 607/34, 57, 32, 60

(56) References Cited

U.S. PATENT DOCUMENTS

| | | | |
|---|---|---|---|
| 4,134,408 A | * 1/1979 | Brownlee et al. | 607/33 |
| 4,408,607 A | 10/1983 | Maurer | 607/61 |
| 5,372,605 A | * 12/1994 | Adams et al. | 607/5 |
| 5,405,363 A | * 4/1995 | Kroll et al. | 607/5 |
| 5,702,431 A | * 12/1997 | Wang et al. | 607/61 |
| 5,713,939 A | * 2/1998 | Nedungadi et al. | 607/33 |
| 5,733,313 A | 3/1998 | Barreras, Sr. et al. | 607/33 |

FOREIGN PATENT DOCUMENTS

| | | | |
|---|---|---|---|
| JP | 640662 | 9/1995 | A61N/1/378 |
| JP | 965635 | 9/1998 | A61N/1/378 |
| WO | WO9906108 | 2/1999 | A61N/1/378 |

OTHER PUBLICATIONS

*Renew Neurostimulation System* User's Guide, by Advanced Neuromodulation Systems, Inc., copyright Mar., 1999.

* cited by examiner

Primary Examiner—Carl Layno
(74) Attorney, Agent, or Firm—Banner & Witcoff, Ltd.

(57) ABSTRACT

An apparatus and method that will allow for external communication, via an external programmer, for positive device identification and for retrieval of device or patient information stored by an implantable medical device with a depleted power source. The external programmer will deliver energy to a secondary power source located inside the implanted device using RF telemetry sufficient to charge up the secondary power source, e.g., a small capacitor. The capacitor will charge up immediately within milliseconds. Once the secondary power source is sufficiently charged, it can be used to power up a controller having the stored information in the implantable medical device. Once the controller is operational, the implanted device will transmit device and patient information to the external programmer via RF telemetry.

51 Claims, 8 Drawing Sheets

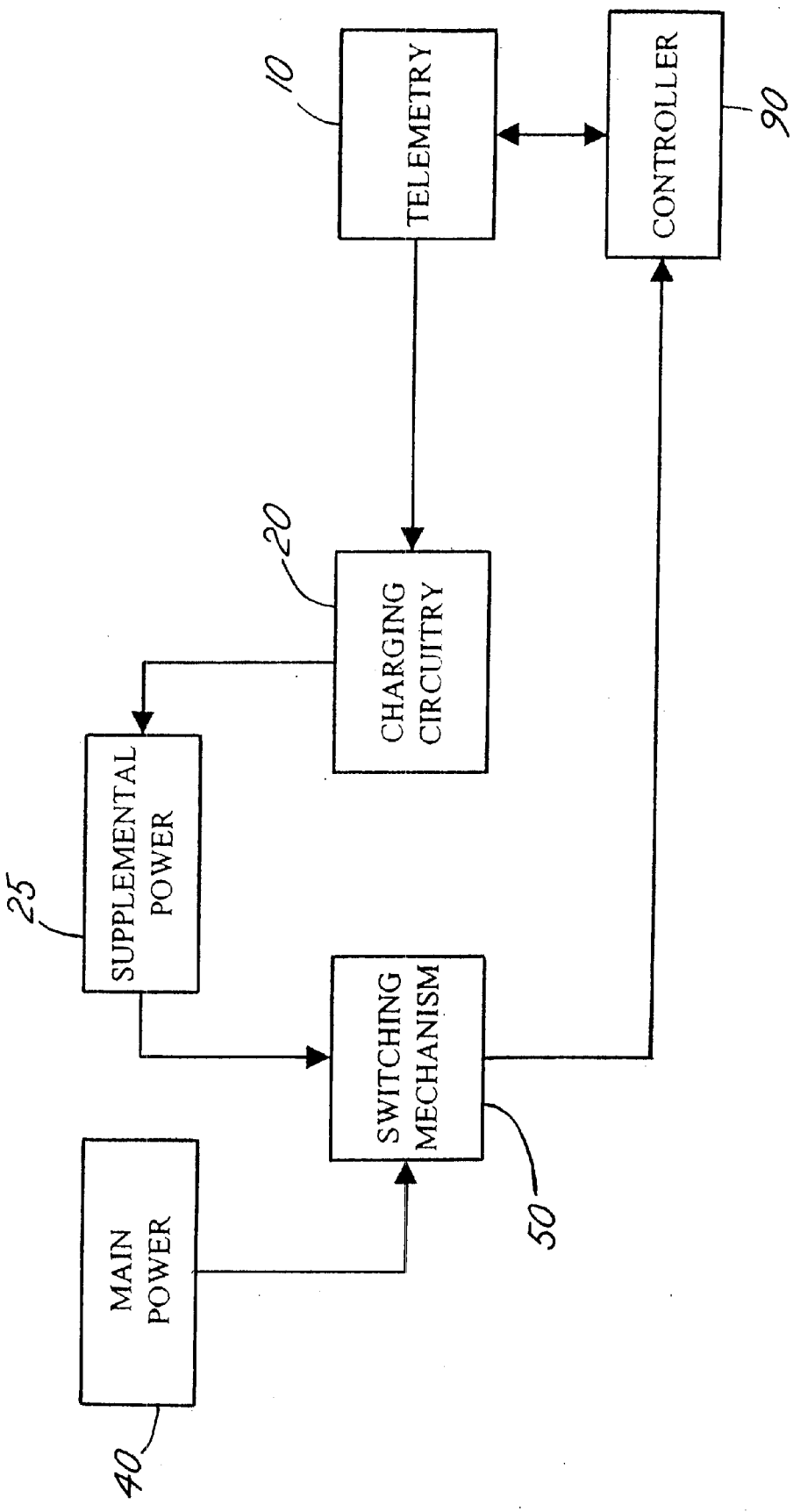

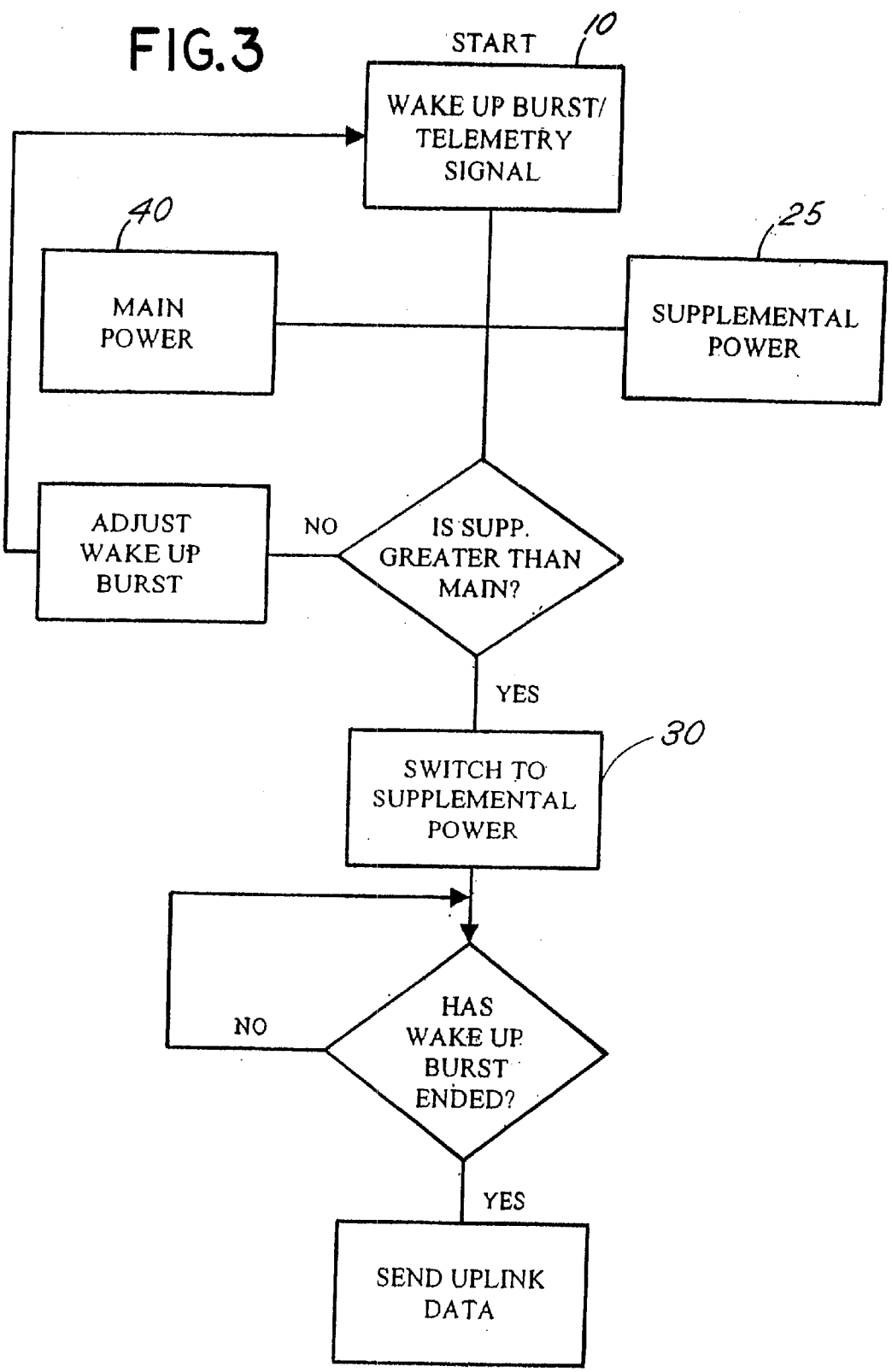

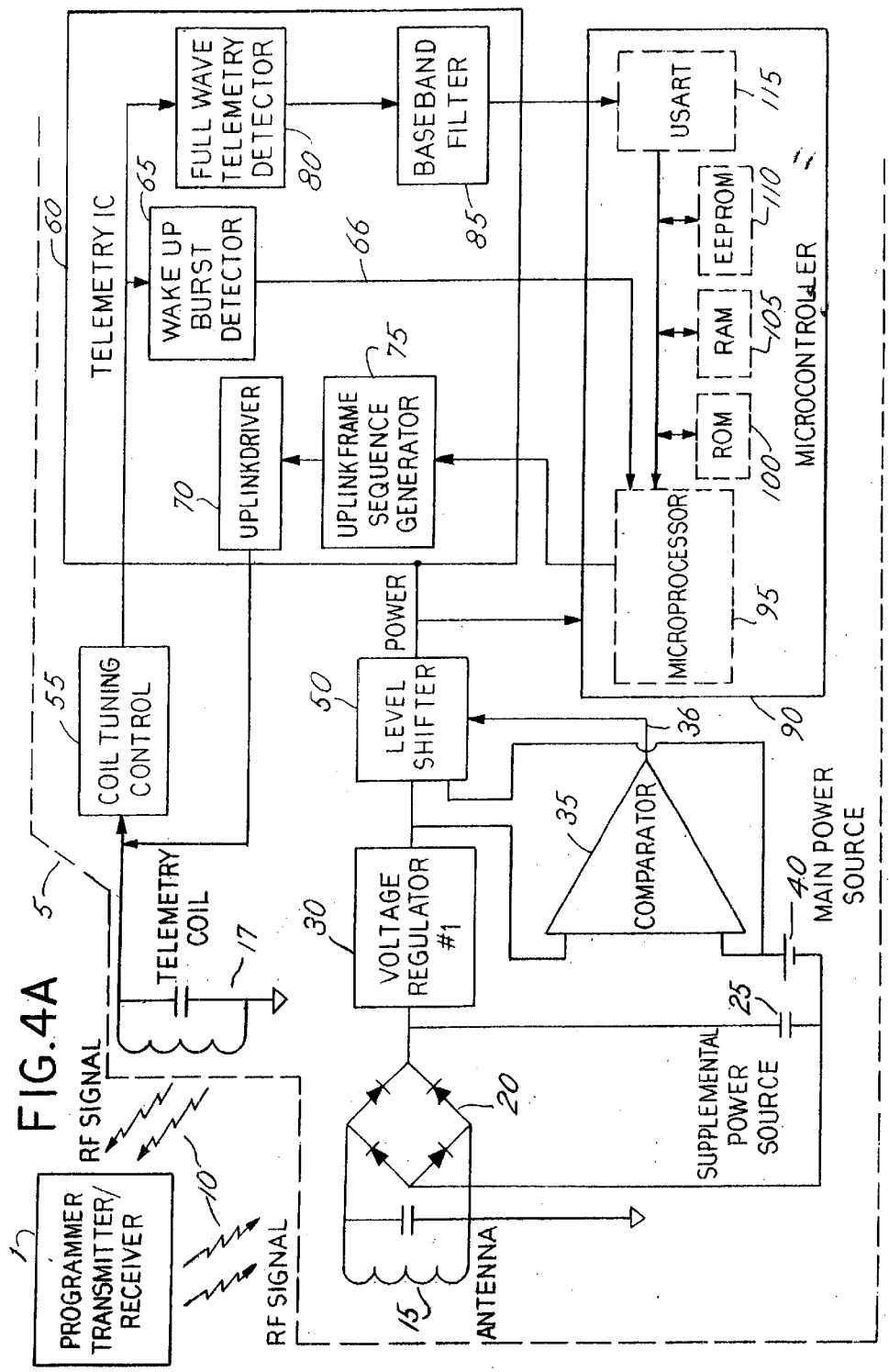

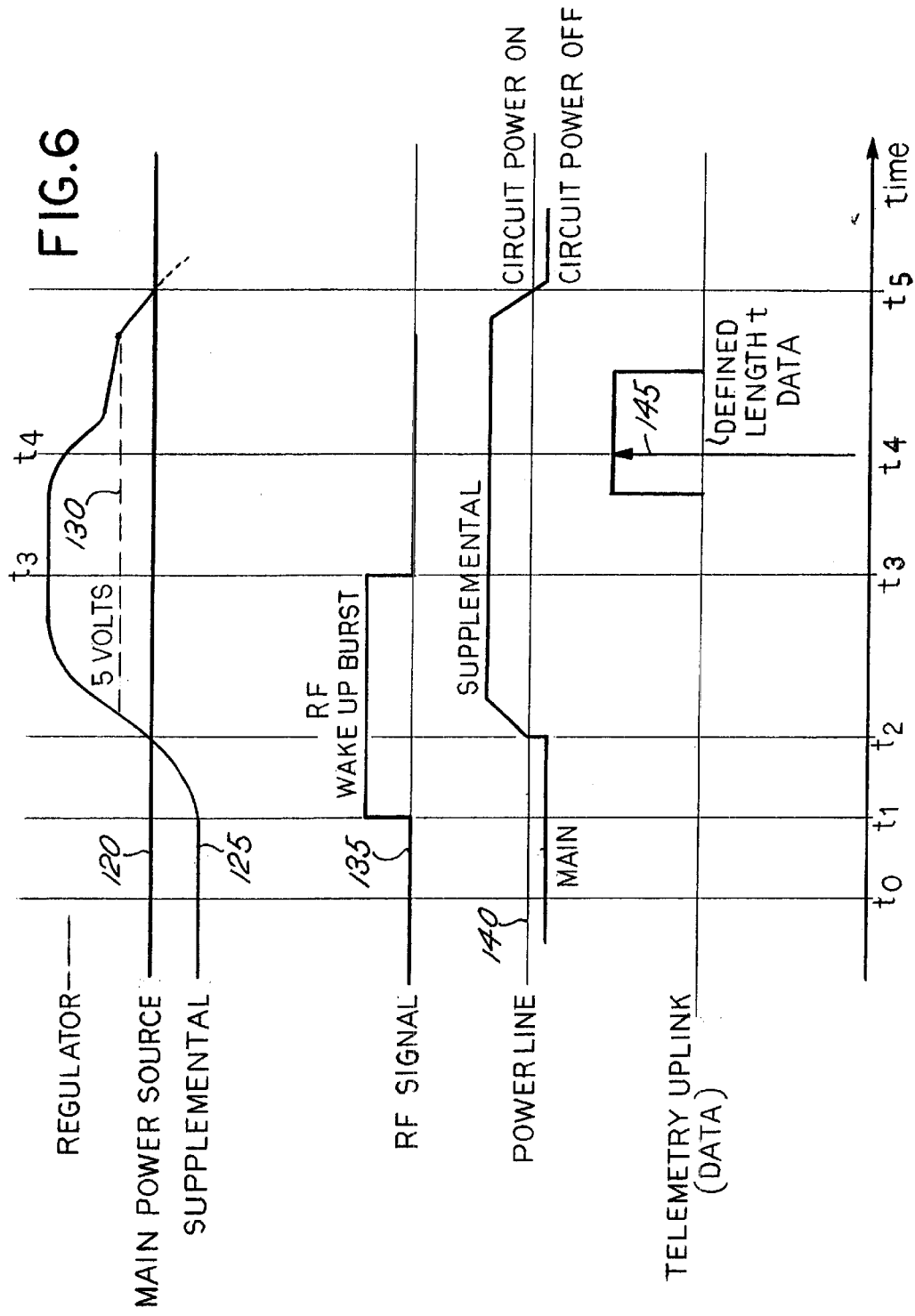

APPARATUS AND METHOD FOR ALLOWING IMMEDIATE RETRIEVAL FOR INFORMATION AND IDENTIFICATION FROM AN IMPLANTABLE MEDICAL DEVICE HAVING A DEPLETED POWER SOURCE

FIELD OF INVENTION

The present invention relates generally to medical implantable devices. More particularly, the invention relates to implantable medical devices that are able to communicate device identification parameters and information, as well as patient information, even when the implanted medical device has a depleted power source.

BACKGROUND OF THE INVENTION

Implantable medical devices are used to treat patients suffering from various ailments. Some of the more common forms of implantable medical devices are implantable neurological stimulation devices, pacemakers, defibrillators and implantable drug delivery systems. For example, implanted neurological stimulator devices are used to treat patients suffering from such ailments as chronic pain, movement disorders, and incontinence.

A pacemaker is generally used to properly stimulate the heart when the body's natural pacemaker malfunctions, due to age or disease. The pacemaker will deliver electrical pulses to an electrode that is implanted adjacent the patient's heart in order to stimulate the heart so that it will beat at a desired rate.

Implantable defibrillators are used with patients prone to ventricular fibrillation. The implantable defibrillator senses physiological parameters and determines when to supply a defibrillating shock to a patient's heart in an effort to overwhelm the unusual contractions of individual tissue sections and to restore the synchronized contraction of the total mass of heart tissue.

Implantable drug delivery systems provide stored drugs to target sites of patients. Implantable drug delivery systems usually rely upon physiological parameter sensors to provide signals that may be processed internally in order to determine when, and in what amount to deliver a drug dosage.

There are a myriad of other implantable medical devices available to patients today. The aforementioned devices are merely some of the more common devices in the medical field.

Existing implantable medical devices typically include a controller with memory, two way-communication capability, electrical circuitry and components, a therapy program, and an internal power source. The internal power source can be either a rechargeable or a non-rechargeable power source. Existing implantable medical devices typically have the ability to gather and process data relating to the patient's physiological parameters. In this manner, the implanted medical device can determine when and what actions to take to address the needs of the patient. Existing implantable medical devices typically have two-way communications, such as a telemetry communication link, to communicate the gathered and stored data to the outside world. In this manner, patient information can be retrieved from the implanted medical device thereby allowing medical personnel to evaluate information relating to the status of a patient. Additionally, information relating to the identification and status of the implantable device itself can be retrieved from the implanted device. The two-way communication also allows medical personnel to transmit or deliver updated operating instructions to the implantable medical device to address any possible problems indicated by the retrieved physiological parameters or update the device parameters. Therefore, the ability to communicate with the implantable medical devices and extract or retrieve information, both device specific information and patient physiological information, is crucial in determining the appropriate treatment of the patient.

Existing implanted medical devices, as just described above, generally have a single power source. A drawback of existing implantable medical devices is that all external communication is lost when the single power source of the device is depleted. When the power source of the device is depleted, medical personnel are unable to communicate with the device. Under the circumstances in which these devices are used, it is important that some external communication be maintained and/or reestablished with the device to determine the physiological condition of the patient for appropriate patient diagnosis and treatment. Additionally, existing devices do not have the ability to communicate device identification and device information to the outside world once the power source is depleted.

Medical personnel need to have the ability to identify what type of device is in use before taking any action and administering any form of treatment to the patient. For example, some devices use a rechargeable main power source while others use a non-rechargeable main power sources. As such, there is a need to know, prior to administering medical assistance, what type of device is involved. Presently, this situation requires that patient files be located, X-rays taken to identify the implanted medical device, or in a worst case, that the device be removed for identification prior to rendering medical attention to the patient. Otherwise, incorrect medical assistance may result since it is unknown exactly what type of device is implanted in the patient if medical records are unavailable. This process takes time, which depending on the situation, may not be available due to the patient's condition.

Other implantable medical devices use both rechargeable and non-rechargeable power sources simultaneously. In these types of devices, the non-rechargeable part of the power source is used to power the controller operating the implanted device since the power consumption of the controller is minimal, thereby allowing the controller to operate for a long period of time. In these types of devices, the rechargeable power source is used as the power source for the electrical stimulating pulses that are applied to the patient, since the pulses require more power than the controller. Feeding the electrical stimulating pulses from a separate rechargeable power source gives the implantable medical device a longer operating life. The timing, power and duration of the therapy pulses is controlled by the controller. However, when the non-rechargeable power source feeding the controller is depleted, there exists the same problem as described above, i.e., external communication with the implantable medical device is lost with no immediate way of identifying the implanted device or the condition of the patient from the implanted device.

Still other types of devices attempt to avoid the problem just described by avoiding a depleted power state altogether. These devices may employ design circuitry that will allow the implantable medical device to communicate a warning signal to the patient or medical personnel that a low critical power level is being approached so that precautionary steps may be taken. However, these devices too, lose the ability to communicate externally when power is depleted.

Thus, conventional implantable medical devices do not provide an apparatus or method to immediately energize a controller and retrieve device information and identification from an implantable medical device with a depleted power source.

SUMMARY OF THE INVENTION

The present invention provides an apparatus and method that allows external communication for positive device identification and for retrieval of device and patient information from an implantable medical device with a depleted primary or main power source. The apparatus and method of the present invention will allow an external programmer to immediately re-energize, within milli or micro seconds, the implantable medical device and subsequently retrieve device and patient information.

In accordance with the present invention, should the primary or main power source of an implantable medical device become depleted, an external programmer can deliver energy to a secondary or supplemental power source in the implantable medical device using telemetry, and preferably radio frequency ("RF") telemetry. The energy transmitted via telemetry is sufficient to charge up the secondary or supplemental power source comprised of either a small capacitor, a rechargeable battery or other rechargeable energy storage device. Once the secondary power source is sufficiently charged, the secondary power source can be used to power up internal circuitry and a controller in the implantable medical device.

Once the internal circuitry and controller are operational, the implanted device can transmit information back to the external programmer via telemetry, including model identification information, type of primary or main power source used, patient information or any other desired information. The implantable medical device can then power down, since the secondary or supplemental power source is preferably large enough to allow the controller to temporarily operate and then transmit patient and device information to medical personnel. Use of the supplemental power source is preferably needed when the primary or main power source is depleted and retrieval of information is required prior to rendering medical attention or assistance. Otherwise the implantable medical device normally operates from the primary or main power source of the implantable medical device.

The present invention is viable whether the medical device uses a rechargeable or nonrechargeable battery as its primary or main power source. This is especially beneficial when the course of medical action to be taken depends on whether the power source is of the rechargeable or non-rechargeable type. If, for example, the medical device has a rechargeable power source, then the present invention will immediately identify it as such, and the rechargeable power source can be recharged. On the other hand, if the device is identified as being of the non-rechargeable variety, then recharging would not be an option and an alternate course of action can be taken. Without the present invention, the identification of the implantable medical device can take a longer period time and/or result in confusion or mistake as to what type of power source is being used.

Thus, it is an object of the present invention to provide an apparatus and method for the immediate reenergization of an implantable medical device having a depleted main power source and for the retrieval of device identification, device information and patient information, and further to do so within a short period of time, i.e., milli or micro seconds.

It is also an object of the present invention to provide an apparatus to allow for the retrieval of device identification, device information and patient information from an implantable medical device having either a depleted rechargeable or depleted non-rechargeable main power source.

It is a further object of the present invention to provide an apparatus to allow for the retrieval of device identification device, information and patient information from an implantable medical device having a depleted main power source through the use of telemetry communication.

It is a further object of the present invention to provide an apparatus to allow for the immediate retrieval of device identification, device information and patient information from an implantable medical device having a depleted main power source through the use of an RF external programmer.

It is also a further object of the present invention to provide an apparatus that will allow for the storage of energy that is transmitted via electromagnetic waves, such as in RF signals. In accordance with the present invention, the energy in the RF signals is stored in an energy storage component or device, or supplemental power source. In this manner the energy storage device or supplemental power source will be able to temporarily provide electrical power to the electrical and electronic components of the implantable medical device. In this manner, the temporarily powered medical device can communicate gathered and stored data to the outside world or receive information from the outside world via telemetry, e.g., RF signals.

It is also a further object of the present invention to provide a method for the storage of energy that is transmitted via electromagnetic waves, such as RF signals. In accordance with the present invention, energy transmitted via the RF signals is stored in an energy storage component or device. The energy storage device will then be able to temporarily provide power to the electrical and electronic components when the main power source is depleted. Information relating to the medical device can then be retrieved from, or delivered to the device via RF signals.

BRIEF DESCRIPTION OF THE DRAWINGS

FIG. 2 depicts a block diagram of certain components of a preferred embodiment of the present invention.

FIG. 3 depicts is a logic flowchart of certain steps which determine a power supply source for a controller in a preferred embodiment of the present invention.

FIG. 4A depicts a block diagram representation of a preferred embodiment of the present invention connected to an implantable medical device having a non-rechargeable main power source, and separate recharge and telemetry coils.

FIG. 6 depicts timing diagrams of certain components relative to a horizontal time axis used in a preferred embodiment of the present invention.

DESCRIPTION OF THE PREFERRED EMBODIMENTS

Figure 1A:
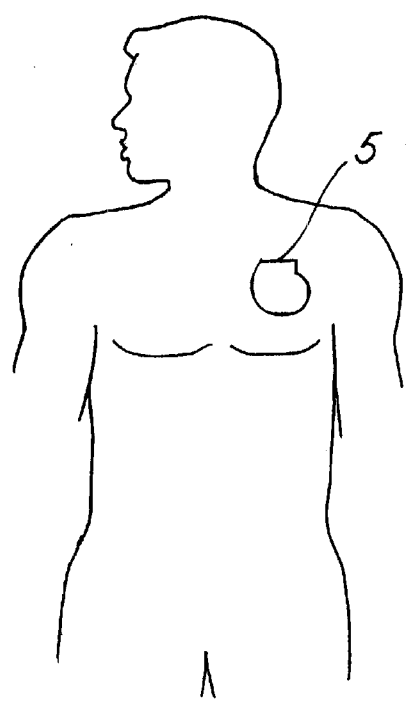
FIGS. 1A–1D depict implantable medical devices in various parts of the human body in which embodiments of the present invention could be used.
Figure 1B:
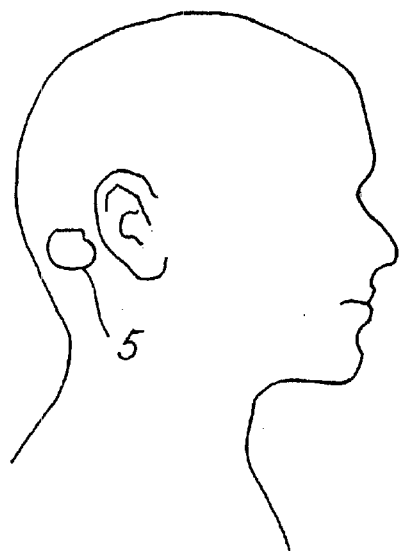
Figure 1C:
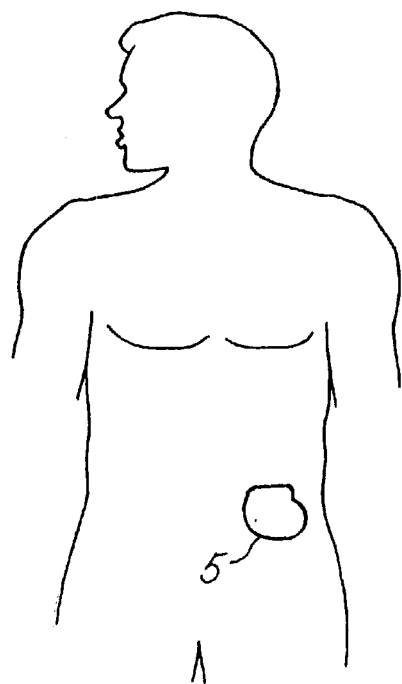
Figure 1D:
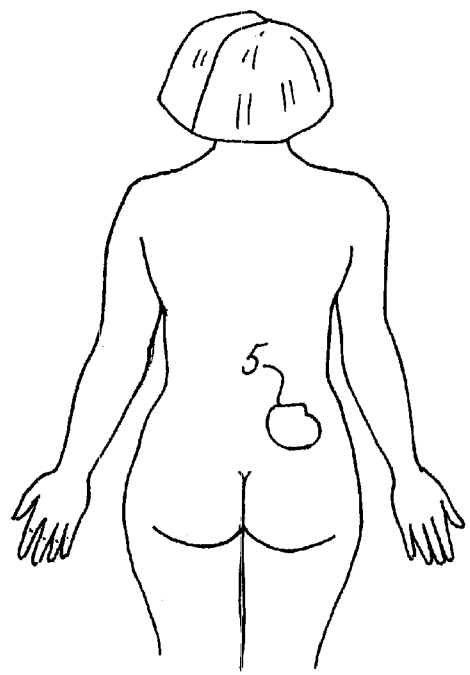

FIGS. 1A–1D illustrate visually where implantable medical devices 5 may be implanted in the human body. Each implantable medical device 5 is placed in the human body to deliver medical treatment. Typically, such medical devices 5 deliver electrical pulses as therapy or they may deliver predetermined doses of medicine to the patient. It is envisioned that such implantable medical devices 5, as well as other types of implantable medical devices 5, can comprise a supplemental power source in accordance with the present invention.

FIG. 2 depicts a block diagram of a preferred embodiment of the present invention. In block diagram form, FIG. 2 illustrates that a telemetry signal 10 interacts directly with a charging circuit 20 and a controller 90. Electromagnetic energy in the telemetry signal 10 allows the charging circuit 20 to charge up the supplemental power source 25. The telemetry signal 10 also interacts with the controller 90 to deliver and receive patient and device data. Under normal operating conditions, the main power source 40 has a larger voltage value than the supplemental power source 25. Thus, under normal operating conditions, the switching mechanism or level shifter 50 operates so that it is the main power source 40 is being fed through the switching mechanism 50 to the controller 90. When the main power source 40 has been depleted, the implantable medical device 5 (not shown in FIG. 2) is no longer operational. For purposes of the present invention, the main power source 40 is considered depleted when the voltage level of the main power source 40 drops below a working voltage level that will energize or operate the circuitry and electrical components in the implantable medical device 5. The working voltage level of typical implantable medical devices can range from 1.0 to 3.0 volts. When the main power source 40 is depleted, a telemetry signal 10 can deliver sufficient energy to the supplemental power source 25, through the charging circuit 20, to temporarily revive the inoperable implantable medical device 5. Under these conditions, i.e., a depleted main power source 40, the supplemental power source 25 will have a larger voltage value than the main power source 40. More specifically, under these conditions, the switching mechanism 50 will allow power to be fed from the supplemental power source 25 to the controller 90. The supplemental power source 25 will have sufficient power to activate the controller 90 such that information or data relating to the patient and the implantable medical device 5 can be transmitted within milli or micro seconds, via telemetry 10, to an external programmer (shown in FIGS. 4 and 5). With pertinent information in hand, medical personnel can then take the appropriate actions for a particular patient. Once the controller 90 has transmitted its data, the implantable medical device 5 can power down.

Figure 4:
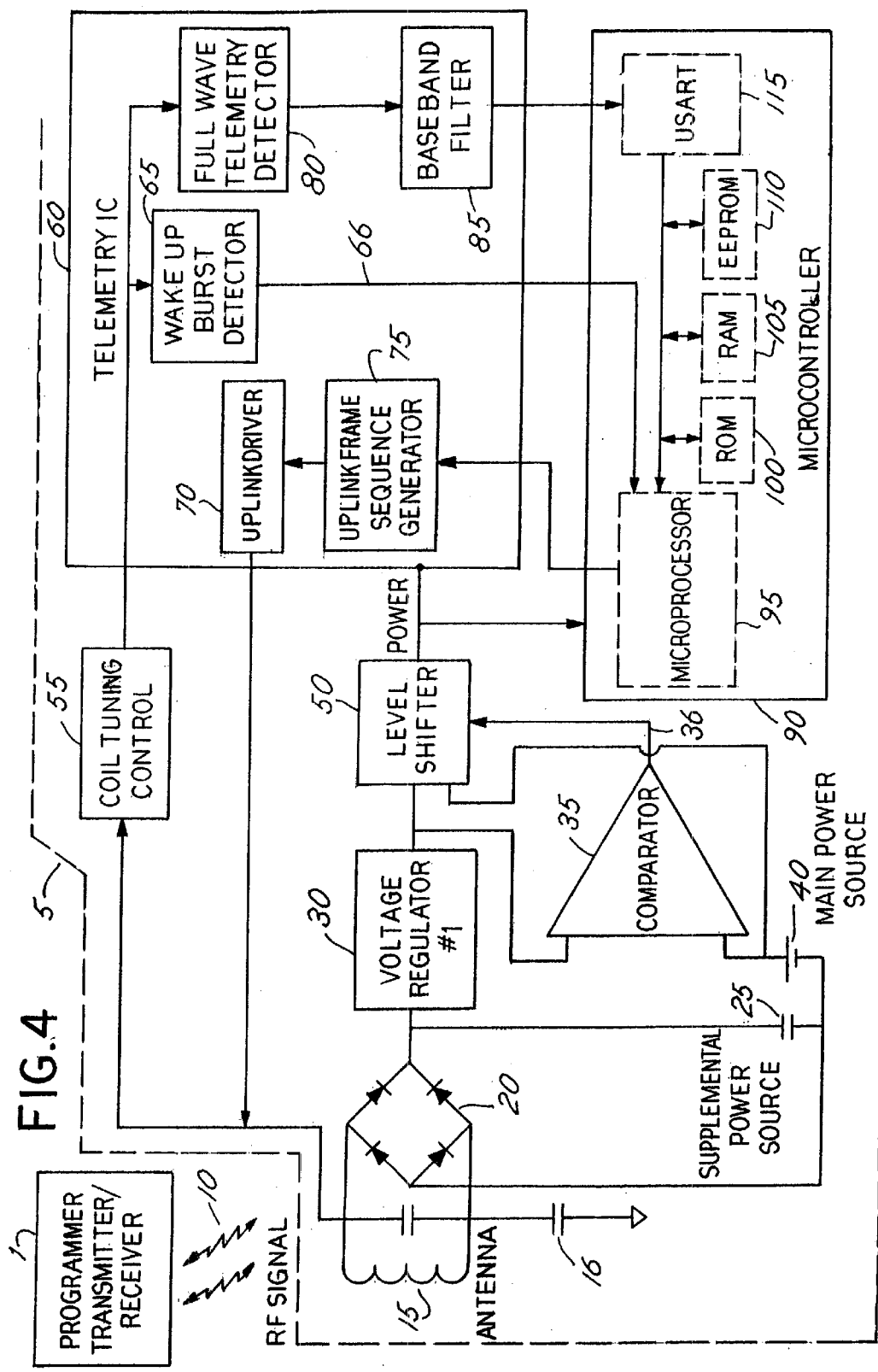
FIG. 4 depicts a block diagram representation of a preferred embodiment of the present invention connected to an implantable medical device having a non-rechargeable main power source.
Figure 5:
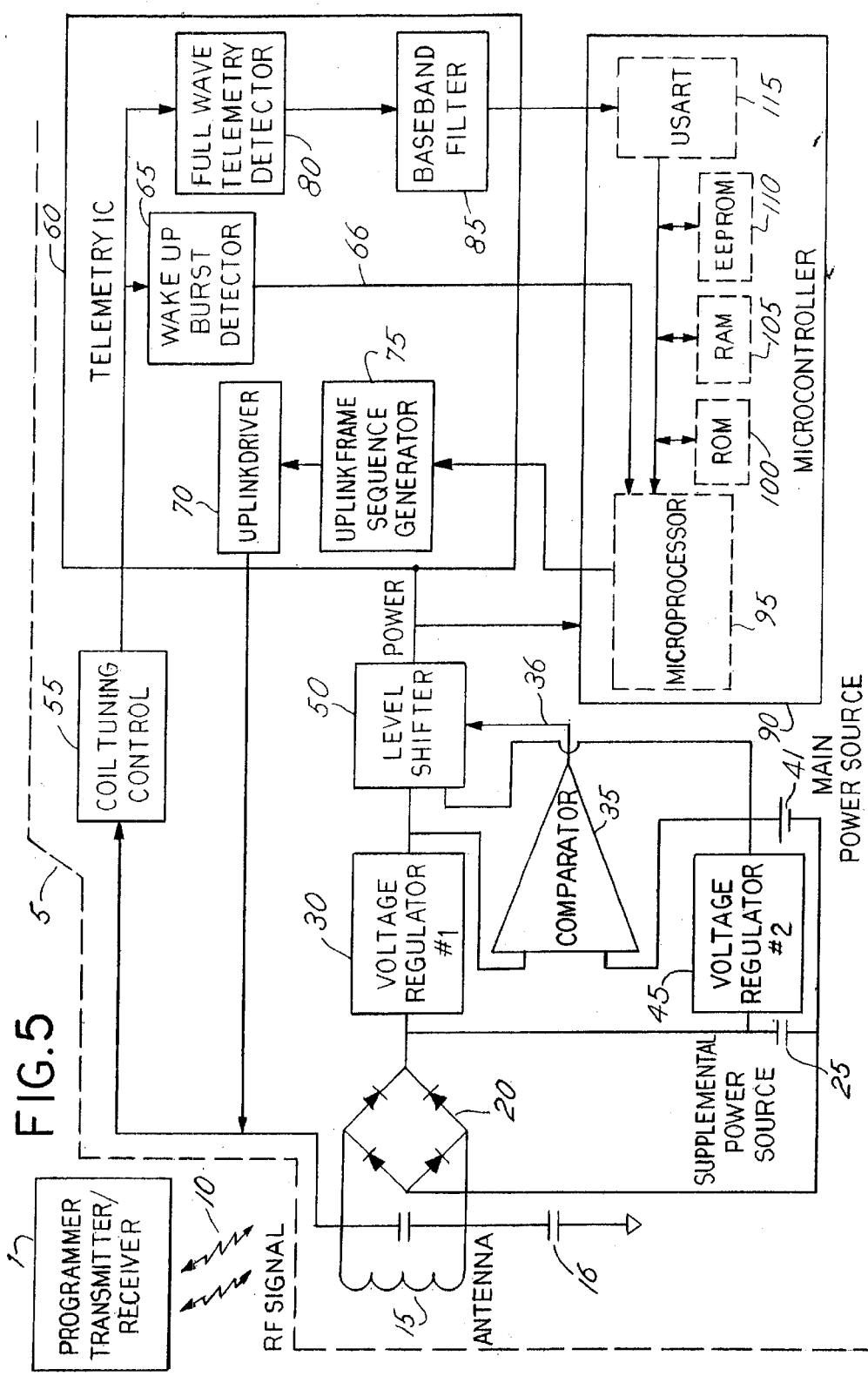
FIG. 5 depicts a block diagram representation of a preferred embodiment of the present invention connected to an implantable medical device having a rechargeable main power source.

FIG. 3 is a logic flowchart of a preferred embodiment of the present invention that illustrates when supplemental power is to be fed to the controller 90 (shown in FIGS. 4 and 5) so that patient and device data can be transmitted/uplinked to an external programmer 1 (shown in FIGS. 4 and 5). First, a wake up burst signal is delivered to the medical device. A comparator 35 (shown in FIGS. 4 and 5) then compares the voltage values of the main power source and the supplemental power source. If the supplemental power source voltage is not greater than the main power source voltage, the wake up burst or telemetry signal strength is adjusted, by increasing the signal strength or the length of the wake up burst, and repeated. When the supplemental power source is greater than the main power source, a level shifter 50 (shown in FIGS. 4 and 5) will select the power feed from the supplemental power source. This power feed will continue until the wake up burst signal has terminated. At that point, patient and device data can be prepared and transmitted to an external programmer 1 (shown in FIGS. 4 and 5), the implantable medical device 5 (shown in FIGS. 1, 4 and 5) can then power down.

FIG. 4 shows, in greater detail, a block diagram representation of a preferred embodiment of the present invention which allows external communication of an implantable medical device 5 having a non-rechargeable depleted main power source 40 with an external programmer 1 for retrieval of device identification, device information and patient information. The apparatus and method of the present invention will allow an external programmer 1 to immediately re-energize the implantable medical device 5 within milli or micro seconds and subsequently retrieve device identification, device information and patient information. In this preferred embodiment, the implantable medical device 5 comprises antenna 15, a telemetry integrated circuit ("IC") 60, a controller 90, a comparator 35, a main power source 40, a level shifter 50, a first voltage regulator 30, a bootstrap or supplemental power source 25, a rectifier circuit 20, and a filter 16. Those skilled in the art will readily appreciate that filter 16 is a typical low frequency high impedance element, which will allow different telemetry frequencies to be used for different applications. A lower frequency signal could be used for supplying power to the supplemental power supply while a higher frequency could be used for communication purposes when the implantable medical device 5 has enough functional power supplied by the main power source.

As shown in FIG. 4, the implantable medical device 5 has an antenna 15 that is electrically connected to a rectifier circuit 20, a filter 16, a coil tuning control 55 that is connected to a wake up burst detector 65, and to an uplink driver 70. The rectifier circuit 20 is electrically connected to a secondary or supplemental power source 25. In the preferred embodiment shown, the supplemental power source 25 is an energy storage device that may be comprised of a small capacitor of a predetermined size in the microfarad ($\mu$F) range of 5–15 microfarads, or rechargeable batteries. The supplemental power source 25 is connected to a first voltage regulator 30, which maintains the voltage of the supplemental power source 25 within a predetermined voltage in the range of about 2.0–5.0 Volts, and preferably 3.0 Volts. The first voltage regulator 30 is electrically connected to both a comparator 35 and a level shifter 50. As previously stated, the implanted medical device 5 also has a primary or main power source 40. Under normal operating conditions, it is the main power source 40 that operates the implantable medical device 5. The main power source 40 is also electrically connected to the comparator 35 and the level shifter 50. The level shifter 50, through which power is delivered, is then electrically connected to the telemetry integrated circuit (IC) 60 and the micro controller 90.

Micro controller 90 comprises a controller 95, memory, both read only memory ("ROM") 100 and random access memory ("RAM") 105, an electronically erasable read only memory ("EEPROM") 110, and a universal synchronous/asynchronous receiver/transmitter ("USART") 115. In the preferred embodiment, the controller 90 used in the present invention may be a microprocessor, an application specific integrated circuit (ASIC) state machine, a logic gate array or other logic circuitry that can appropriately carry out the desired functions of the implantable medical device. The controller 90 controls and operates the implantable medical device 5. As shown in FIG. 4, the controller 95 is electrically connected to the wake up burst detector 65 located the telemetry IC 60, the ROM 100 and RAM 105, the EEPROM 110 and the USART 115. Controller 95 further drives the uplink frame sequence generator 75 in the telemetry IC 60.

A telemetry IC 60 is generally comprised of a wake up burst detector 65, an uplink driver 70, an uplink frame sequence generator 75, a full wave telemetry detector 80, and a baseband filter 85. In this preferred embodiment, the antenna 15 is connected to a coil tuning control 55 which is electrically connected to the wake up burst detector 65 and full wave telemetry detector 80 in the telemetry IC 60. The wake up burst detector 65 is further electrically connected to the controller 95. The full wave telemetry detector 80 is connected to the baseband filter 85 which is further connected to the USART 115. The USART 115 is in turn also electrically connected to the controller 95. The controller 95 is connected to the uplink frame sequence generator 75 which is in turn connected to the uplink driver 70. The uplink driver is finally connected back to the antenna 15.

The implantable medical device 5 of the present invention normally operates with electrical power from its main power source 40. During normal operation of the implantable medical device 5, i.e., when the main power source is not depleted as previously discussed, the main power source 40 has a higher voltage value than the supplemental power source 25. The comparator 35 thus outputs the appropriate electrical signal via electrical connection 36 to the level shifter 50 which in turn selects the main power source 40 as the power feed to the telemetry IC 60 and the micro controller 90. The implantable medical device 5 can transmit information to and receive information from an RF programmer 1, through the antenna 15 via RF telemetry signals 10. After prolonged use, the main power source 40 becomes depleted of electrical power, i.e, has a voltage level less than 1.8 Volts. At this point, a typical implantable medical device 5 will cease to operate and will lose the capability for external communication.

The present invention allows an RF programmer 1 to retrieve device and patient information when the implantable device 5 has a depleted main power source 40 by temporarily providing power to the implantable medical device 5 through radio frequency (RF) coupling/RF telemetry 10 which allows communication to and from the implantable medical device 5. This is made possible by a novel configuration of a supplemental power source 25, a first voltage regulator 30, a comparator 35 and a level shifter 50. As shown in FIG. 4, the RF programmer 1 transmits a wake up burst RF signal 10 via RF telemetry to communicate with the implantable medical device 5. Electromagnetic energy is delivered as a result of the transmission of RF signals 10. Thus, in attempting to communicate with the implantable medical device 5, the RF programmer 1 is at the same time delivering energy to the implantable medical device 5 via the RF communication signals 10. The energy delivered or transmitted by the wake up burst signals 10 is sufficient to charge up the supplemental power source 25 so that it can temporarily provide power to the implantable medical device 5 in the event that the main power source 40 does not have sufficient electrical power to do so, such that information can be retrieved from the implantable medical device 5.

In the operation of this preferred embodiment, an RF Signal, or wake up burst signal, 10 is transmitted to the implantable medical device 5 from an RF programmer 1. In a preferred embodiment, the wake-up burst signal is transmitted for 2.0–4.0 milliseconds. In addition, in a preferred embodiment, the typical frequencies of the wake up burst signal 10 for energy transferral is in a range of about 5–200 KHz, though any frequency may be used. The wake up burst signal 10 is received by the antenna 15 of the implantable medical device 5. This wake up burst signal 10 is rectified by the rectifier circuit 20 and the wake up burst signal 10 energy is stored by the supplemental power source 25. In this embodiment, the supplemental power source 25 may be a small capacitor with a capacity size in the microfarad range or a rechargeable battery. However, any other energy storage device can be used. The small capacity size allows the implantable medical device 5 to be powered up almost immediately or within in milli or micro seconds from the time the RF signal 10 is introduced. This will allow the user, technical or medical personal, immediate feedback relating to the implantable medical device 5, its status and patient information.

Once the supplemental power source 25 has been sufficiently charged and reaches a certain voltage, the voltage regulator 30 will output a constant voltage to the comparator 35 and level shifter 50. In this preferred embodiment, the voltage can be in a range of between about 2.0–5.0 volts, with a preferred value of about 3.0 volts. The comparator 35 compares the voltage from the first voltage regulator 30 to the voltage of the main power source 40. The comparator 35 will detect a higher voltage from the supplemental power source 25 compared to the main power source 40 when the main power source 40 is in a depleted power state and unable to power the implantable medical device 5. The comparator 35 will now send its output signal 36 to the level shifter 50. The level shifter 50 will determine, from the comparator 35 output signal 36, that the appropriate power source to the internal circuitry, i.e., the telemetry IC 60 and the micro controller 90, is the supplemental power source 25. The power from the supplemental power source 25 will be delivered simultaneously through the level shifter 50 to the telemetry circuitry 60 and the micro controller 90. The micro controller 90 will be powered up in a waiting state since the wake-up burst, i.e., the RF signal 10, is still being delivered by the RF programmer 1. If on the other hand, the main power source 40 is not depleted or has a greater voltage value than the supplemental power source 25, then the implantable medical device is operating normally and the medical device is fed from the main power source 40.

The wake-up burst, or RF signal 10, will then be detected by the wake-up burst detector 65, which will send an interrupt to the controller 95. The wake-up burst signal 10 is transmitted for about 2.0–4.0 milliseconds. At this point, the electrical connection interrupt line 66 to the controller 95 enters a high or active state due to the RF transmissions 10 from the RF programmer 1. When the wake-up burst signal 10 is no longer being delivered by the RF programmer 1, the interrupt line 66 from the wake-up burst detector 65 will be in a low or inactive state. Once the controller 95 has sensed a high or active state in the wake-up burst interrupt line 66, the controller 95 will assemble and send device and status information relating to the implanted medical device 5 to the uplink frame sequence generator 75. The telemetry IC 60 will then assemble and send, the device and status information, via the uplink frame sequence generator 75, to the uplink driver 70. The uplink driver 70 will then drive the antenna 15, transmitting RF telemetry signals 10 back to the RF programmer 1. These transmitted RF signals 10 from the medical device 5 communicate device and status information. Such information can include device model number, main power source 40 status, patient condition or any other desired information. The supplemental power source 25 will have enough energy stored to keep the implantable medical device 5 powered until the implantable medical device 5 identification transmission is complete. The implantable medical device 5 can then power down or be turned off. This is the case since the supplemental power source 25 is only intended to be sufficient to allow the telemetry IC 60 and microcontroller 90 circuitry to turn ON and OFF in a controlled manner such that information can be retrieved.

The component configuration of the present invention shown in FIG. 1 has several advantages over conventional devices. The present invention allows rapid recoverability, within milliseconds or even microseconds from the time the wake-up burst is transmitted, of device identification and stored information. The present embodiment will allow the user or medical personnel to determine whether the main power source used in the implantable medical device 5 is of the rechargeable or non-rechargeable type while the device is implanted in a patient, even when the primary power source 40 is in a depleted state. The ability to learn the type of power source used in the implantable medical device 5 helps medical personnel avoid possible mix-ups or confusion of medical procedures which may be specific to a certain type of power sources.

In addition, the present embodiment may, with the appropriate power connection to the level shifter 50, also be used to temporarily power the implantable medical device 5 to a level of full functionality. This advantageous feature allows medical personnel to, in addition to retrieving information and data, analyze and reset patient parameters of an depleted implantable medical device 5. Once the setting changes are complete and permanently stored, the RF programmer 1 can be removed and the implantable medical device 5 would be powered down. Those of skill in the art will recognize that the appropriate power connection to the level shifter 50 can be typical power connections.

FIG. 4A shows a block diagram representation of an alternate preferred embodiment of the present invention that is similar to the embodiment shown in FIG. 4 except for the antennas. The embodiment of FIG. 4A shows a separate recharge coil 15 and telemetry coil 17, unlike the embodiment shown in FIG. 4 which has a combined recharge and telemetry coil 15. The telemetry signal 10 emanating from the external programmer 1 to the separate recharge 15 and telemetry coils 17 is the same signal 10. In this embodiment, the recharge coil 15 is used specifically to recharge the supplemental power source 25, while the telemetry coil 17 is used for telemetry communication purposes. Additionally, this embodiment does not requires a filter 16 as in the previous embodiment of FIG. 4. This embodiment operates similarly in all other respects, as that discussed regarding FIG. 4.

FIG. 5 shows a block diagram representation of an alternate preferred embodiment of the present invention which also allows external communication of an implantable medical device 5 having a depleted main power source 40 with an external RF programmer 1 for retrieval of device identification and patient information. However, in the embodiment of FIG. 5, the main power source 41 is a rechargeable power source, in contrast to the non-rechargeable power source 40 shown in FIG. 4. The alternate apparatus and method of the present invention, using the rechargeable main power source 41, is very similar to that just described with respect to a non-rechargeable main power source 40. The alternate preferred embodiment of the present invention also allows an external RF programmer 1 to immediately re-energize the implantable medical device 5 within milliseconds and subsequently retrieve device and patient information. In this version of the invention, the implantable medical device 5 is comprised generally of an antenna 15, a filter 16, a telemetry IC 60, a micro controller 90, a comparator 35, a rechargeable main power source 41, a level shifter 50, a first voltage regulator 30, a second voltage regulator 45, a bootstrap or supplemental power source 25, and a rectifier circuit 20.

The alternate embodiment of the present invention is identical to the preferred embodiment of FIG. 4 with the addition of a second voltage regulator 45 and the use of a rechargeable main power source 41 instead of a non-rechargeable power source 40 (shown in FIG. 4). The implanted medical device 5 shown in FIG. 5 has an antenna 15 that is connected to a rectifier circuit 20, a filter 16, a coil tuning control 55 that is connected to a wake-up burst detector 65 and a full wave telemetry detector 80, and to an uplink driver 70. The rectifier circuit 20 is connected to a bootstrap or supplemental power source 25, and a first and second voltage regulator 30 and 45. In this embodiment, the supplemental power source 25 may again be a small capacitor of a predetermined size in the microfarad ($\mu$F) range or a rechargeable battery, as in the embodiment described with respect to FIG. 1. The supplemental power source 25 is connected to a first voltage regulator 30 which maintains the voltage of the supplemental power source 25 at a predetermined range of about 2.0–5.0 volts, preferably at 3.0 volts. The first voltage regulator is connected to both a comparator 35 and a level shifter 50. There is also a second voltage regulator 45 which is connected to the rectifier circuit at one point, and to the comparator 35, the rechargeable main power source 41 and the level shifter 50 at another point. The second voltage regulator 45 will assure that a constant voltage is fed from the rechargeable main power source 41 to the comparator 35 and the level shifter 50.

The alternate embodiment, shown in FIG. 5, allows for communication to and from the implantable medical device 5 when the rechargeable main power source 41 has been depleted or when the voltage of the main power source 41 is below a predetermined level voltage (preferably 3.0 volts) during recharging. If the main power source 4l is below the predetermined level, then as before, the comparator 35 will send its output signal 36 to the level shifter 50 indicating to the level shifter 50 that the appropriate power feed to the internal circuitry, i.e., the telemetry IC 60 and the micro controller 90, is the supplemental power source 25. The use of the rechargeable main power source 41 is similar to the main power source 40 in FIG. 4, but has additional features, e.g., primarily that the main power source 41 can be recharged via RF telemetry signals 10. In all other respects, the alternate embodiment functions like the embodiment described with respect to FIG. 4.

The use of a rechargeable main power source 41 has several advantages, in addition to those already discussed with respect to the embodiment shown in FIG. 4. As already mentioned, the present invention allows rapid recoverability of device identification and stored information from a depleted device 5 using standard telemetry technology, as was the case for a medical device 5 with a non-rechargeable main power source 40. Thus, the present invention allows the user or medical personnel to determine whether the main power source used in the device 5 is of the rechargeable 41 (FIG. 5) or non-rechargeable type 40 (FIG. 4), thus helping to prevent mix-ups or confusion of medical procedures which may be specific to a certain type of power sources.

This embodiment may also be used to temporarily power the implantable medical device 5 to a level of full functionality. Furthermore, the present embodiment of the invention helps the user determine whether the rechargeable main power source 41 of the implantable medical device 5 is depleted, whether recharging is needed, and may also be used to completely recharge the depleted main power source 41.

Figure 5A:
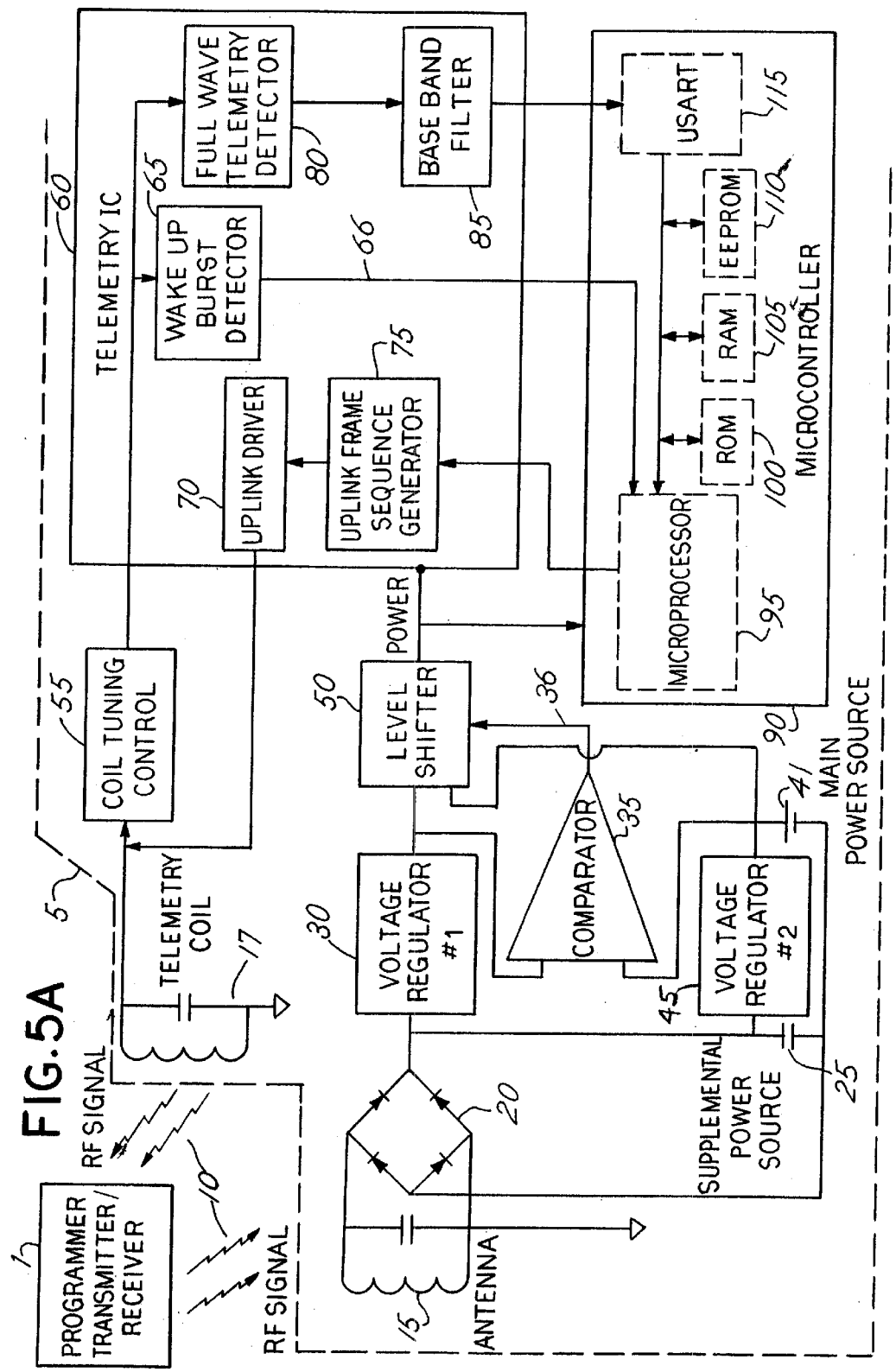
FIG. 5A depicts a block diagram representation of a preferred embodiment of the present invention connected to an implantable medical device having a rechargeable main power source, and separate recharge and telemetry coils.

FIG. 5A shows a block diagram representative of an alternate preferred embodiment of the present invention that is similar to the embodiment shown in FIG. 5 except for the antennas. The embodiment of FIG. 5A shows a separate recharge coil 15 and telemetry coil 17, unlike the embodiment shown in FIG. 5 which has a combined recharge and telemetry coil 15. The telemetry signal 10 emanating from the external programmer 1 to the separate recharge 15 and telemetry coils 17 is the same signal 10. In this embodiment, the recharge coil 15 is used specifically to recharge the supplemental power source 25 and rechargeable main power source 41, while the telemetry coil 17 is used for telemetry communication purposes. Additionally, this embodiment does not require a filter 16 as in the previous embodiment of FIG. 5. This embodiment operates similarly in all other respects, as that discussed regarding FIG. 5.

FIG. 6 illustrates a timing diagram graph versus time of the states of certain components or variables of the present invention once a wake-up burst signal has been initiated. The timing diagram shows a time t0 which correlates to a steady state of a medical device. A reading of the variables at time t0 indicates that the medical device is inactive since the voltage value of the main power source is below the powerline curve 140. At time t0 there is no RF signal, the supplemental power source voltage 125 is less than the main power source 120 and there is no telemetry uplink.

At time t1, an RF signal or wake-up burst 135 is transmitted to the inactive medical device. The supplemental power source 125 instantly begins charging up. The medical device is still inactive since the supplemental power source voltage 125 is still less than the main power source 120 at time t1. Also, at time t1 there is still no telemetry uplink connection.

At a time t2, the wake-up burst signal 135 is still being transmitted and there is no telemetry uplink connection. The supplemental power source voltage 125 has just exceeded the main power source voltage 120. At this point time t2, the medical device becomes active and is now being powered by the supplemental power source, as shown on the powerline curve 140. The supplemental power source 125 continues charging and obtaining a larger voltage value. The voltage level supplied to the medical device from the supplemental power source, however, will be kept constant at a predetermined voltage level by a voltage regulator 130, as shown in the powerline curve 140. This is necessary because the supplemental power source 120 would otherwise obtain large voltage values that could damage the device itself. Thus, the powerline curve 140 shows that the supplemental power source voltage operating the medical device will reach a constant voltage level determined by a voltage regulator. The supplemental power source curve 125, on the other hand, indicates that the voltage level would continue to increase during the wake-up burst signal 135 without a voltage regulator 130.

At time t3, the wake-up burst signal ends 135. At this point, the supplemental power source 125 stops charging and begins a process of voltage decay. The supplemental power source 125 is greater than the main power source 120 and has sufficient power to operate the medical device. Due to the charged supplemental power source, that resulted from the wake up burst, the medical device is now operable.

At time t4, the controller in the medical device has gathered patient and device data and begins to transmit 145 the data via telemetry to an external programmer (not shown). This transmission of data by the controller increases the current drain on the charged supplemental power source. Thus, the supplemental power source voltage 125, which was already decaying prior to time t4, begins to decay at a much faster rate. This is the case because of the transmission of data to the external RF programmer. The increased rate of voltage decay is depicted in the supplemental power source curve 125 at time t4. Once the data has been transmitted, the supplemental power source 125 continues to decay until it falls below a level where the medical device will no longer operate. This is shown on the powerline curve 140 at time t5.

The time line of FIG. 6, thus shows the states and activity of certain components of a preferred embodiments of the present invention operate used to revive a medical device with a depleted power source, retrieve patient and device data, and then power down subsequent to the information retrieval. In this preferred embodiments, the time elapsed between time t0 and time t4 is in the millisecond or microsecond range.

The data retrieval process can be repeated in order to extract larger amounts of information from the implantable device 5. In one method, the external programmer 1 sends another wake-up burst 10 in order to recharge the supplemental power supply 25 before the supplemental power supply 25 completely depletes below the power threshold of the internal circuitry of the implantable medical device 5. In this manner the microcontroller 90 would remember which data it had sent after the previous wake-up burst 10 and send the next block of data. This could be continued until the external programmer 1 is notified, through telemetry, that all of the information requested has been transmitted to the external programmer 1.

Another method for extracting larger amounts of data is to have a "pointer" (not shown) stored in non-volatile memory, such as an EEPROM, every time data is transmitted to the external programmer. In this manner, the implantable device would identify which information had already been sent and which data stills needs to be sent. It would not be necessary to recharge the secondary power source before the secondary power source had depleted its energy, since it would remember which blocks of data were already sent. The marker location in the EEPROM could be reset by the programmer with a telemetry command that would occur after the wake up burst was sent (which charges up the supplemental power supply so that the electronics can detect the telemetry command).

In the preferred embodiments of the present invention, discussed with reference to FIGS. 4 and 5, the full wave telemetry detector 80 and baseband filter 85 can be used to detect other more complex RF signals 10 from the RF programmer 1 besides the simple wake up burst or RF signals 10. The more complex signals transmitted by the RF programmer 1 could request other information from the device, e.g., the battery status, patient information, or set new therapy settings. In such a case, the full wave telemetry detector 80 will detect the more complex telemetry signals 10 and the baseband filter 85 will convert the signals to digital signals that the USART 115 in the micro controller 90 can process. Receiving such signals would change the uplink assembled by the micro controller 90 so that the proper information could be sent to the RF programmer 1.

These and other variations that result in the retrieval of more detailed information will be readily appreciated and understood by those skilled it the art.

In the embodiments of the present invention, discussed with reference to FIGS. 4, 4A, 5, and 5A, voltage regulators are used to maintain the supplemental power source at a predetermined safe voltage limit. However, it will be readily appreciated by those skilled it the art that other components can be substituted for the voltage regulators to limit voltage level. Voltage regulation can also be accomplished through the use of zener diodes or other type of know designs and components that clamp the voltage to a predetermined safe level. For example, a zener diode rated at five volts would drain the necessary current supplied by the rectifier circuit to keep the voltage on the supplemental power source from exceeding five volts and in so doing protect the electronic circuitry int he medical device.

Furthermore, the rectifier circuit 20, shown in FIGS. 4, 4A, 5 and 5A, is a full rectifier having diodes (not shown). Again, other circuits that result in charging the supplemental power source 25 can be used, e.g., a passive design which uses diodes for full or half wave rectification. In addition, an active rectification circuit could also be used. These and other rectification circuits and methods are well known in the art by those persons skilled it the art.

It will also be apparent to those of skill in the art that the arrangement and configuration of electronic components of the present invention, in particular the transmitted RF signals 10, the rectifier circuit 20, the supplemental power source 25, the first voltage regulator 30, the comparator and the level shifter 50, can be used, not just in the case of implantable medical devices, but in any number of devices that use electronic components, micro controllers and a main power source. This arrangement of components can be used in any electronic device that has a depleted main power source in order to revive and temporarily power up such an electronic device. The energy in the transmitted RF signals is stored in an energy storage component in such a manner as to be able to temporarily provide power to electrical and electronic components such that the device can be temporarily operated.

Those skilled in that art will recognize that the preferred embodiments may be altered or amended without departing from the true spirit and scope of the invention. Thus, while various alteration and permutations are possible, the invention is limited only by the following claims and equivalents.

We claim:

1. An implantable medical device comprising:
   a main power source to supply power to the implantable medical device; and
   a supplemental power source comprising an energy storage device for storage of energy transmitted via telemetry signals of sufficient power to permit communication between the implantable medical device and an external programmer via a telemetry signal when the main power source is depleted, thereby allowing the retrieval of identification and information of the implantable medical device and patient.

2. The implantable medical device of claim 3 wherein the voltage regulator is comprised of zener diodes that maintain the voltage level output from the supplemental power source at a predetermined voltage level.

3. The implantable medical device of claim 1 wherein the supplemental power source further comprises a voltage regulator cooperating with the energy storage device to maintain a voltage level output from the supplemental power source of about 2–5 volts.

4. The implantable medical device of claim 3 wherein the energy storage device reaches said sufficient power in about a microsecond to millisecond time frame once the telemetry signal is initiated from the external programmer.

5. The implantable medical device of claim 4 wherein the energy storage device is a capacitor.

6. The implantable medical device of claim 5 wherein the capacitor has a capacity range of about 5–15 microfarads.

7. The implantable medical device of claim 4 wherein the energy storage device is a rechargeable battery.

8. The implantable medical device of claim 5 or 7 wherein the main power source can be either a rechargeable power source or a non-rechargeable power source.

9. The implantable medical device of claim 8 wherein the telemetry signal is a radio frequency signal.

10. The implantable medical device of claim 9 wherein the implantable medical device is a pacemaker, a defibrillator, or a drug delivery device.

11. An implantable medical device comprising:
    an antenna for receiving and transmitting telemetry signals;
    a rectifier circuit connected to said antenna;
    a filter connected to antenna;
    a main electrical power source to supply power to the implantable medical device;
    a supplemental power source, connected to the rectifier circuit, comprising an energy storage device for storage of sufficient energy to provide power to energize the implantable medical device, said energy received via telemetry signals from an external source;
    a comparator, to compare voltage levels of the main power source and the supplemental power source and output a signal indicating which power source is greater; and
    a level shifter operable to receive the output signal from the comparator, whereby the level shifter will permit power to flow from either the main electrical power source or the supplemental power source based on the signal received from the comparator to power the implantable medical device, thereby allowing communication with an external programmer via telemetry retrieval of identification and information of the medical device and the patient.

12. The implantable medical device of claim 11 wherein the supplemental power source further comprises a voltage regulator cooperating with the energy storage device to maintain a voltage level output from the supplemental power source of about 2–5 volts.

13. The implantable medical device of claim 12 wherein the voltage regulator is comprised of zener diodes that maintain the voltage level output from the supplemental power source at a predetermined level.

14. The implantable medical device of claim 12 wherein the energy storage device sufficient power in a microsecond to millisecond time frame once the telemetry signal is initiated by the external programmer.

15. The implantable medical device of claim 14 wherein the energy storage device can be either a capacitor or a rechargeable battery.

16. The implantable medical device of claim 15 wherein the main power source can be either a rechargeable power source or a non-rechargeable power source.

17. The implantable medical device of claim 16 wherein the telemetry signal is a radio frequency signal.

18. The implantable medical device of claim 17 wherein the implantable medical device can be pacemaker, a defibrillator, or a drug delivery device.

19. An implantable medical device comprising:
- an antenna for receiving and transmitting telemetry signals to and from a programmer, said programmer being external to the implantable medical device;
- a rectifier circuit connected to the antenna;
- a filter connected to the antenna;
- a main electrical power source;
- a supplemental power source connected to the rectifier circuit and comprised of an energy storage device to store energy transmitted via telemetry signals;
- a comparator to compare voltage levels of the main power source and the supplemental power source and output a signal indicating which power source has a greater voltage; and
- a level shifter operable to receive the output signal from the comparator and permit power to flow as a result of the signal received to power the device when the main power source is less than the supplemental power source, thereby allowing retrieval of patient and device information from the implantable medical device.

20. The implantable medical device of claim 19 wherein the energy storage device can reach full energy capacity within milliseconds via energy transmitted through radio frequency telemetry.

21. The implantable medical device of claim 20 wherein the energy storage device is a capacitor.

22. The implantable medical device of claim 20 wherein the energy storage device is a rechargeable battery.

23. The implantable medical device of claim 21 or 22 further comprising a voltage regulator cooperating with the supplemental power source to maintain a voltage level output from the supplemental power source of about 2–5 volts.

24. The implantable medical device of claim 23 wherein the rectifier circuit is a passive rectifier circuit.

25. The implantable medical device of claim 23 wherein the rectifier circuit is an active rectifier circuit.

26. The implantable medical device of claim 23 wherein the main power source is a rechargeable power source or a non-rechargeable power source.

27. The implantable medical device of claim 23 wherein the voltage regulator is comprised of zener diodes that maintain the voltage level output from the supplemental power source at a predetermined voltage level.

28. An implantable medical device comprising:
- at least one lead to deliver electrical stimulation pulses to a patient;
- a controller to initiate and control the communication of identification and information of the implantable medical device or the patient to an external programmer;
- a main power source to supply electrical stimulation pulses to the at least one lead; and
- a supplemental power source comprising an energy storage device for storage of energy transmitted via telemetry signals of sufficient power to energize the controller, at the request of the external programmer, and communicate identification and information of the implantable medical device or the patient to the external programmer when the main power source is depleted of power.

29. The implantable medical device of claim 28 wherein the energy storage device stores sufficient power in a microsecond to millisecond time frame through energy received via the telemetry signals from the external programmer.

30. The implantable medical device of claim 29 wherein the telemetry is comprised of radio frequency signals.

31. The implantable medical device of claim 29 wherein the energy storage device is either a capacitor or a rechargeable battery.

32. The implantable medical device of claim 31 wherein the controller communicates device identification and information to the external programmer via telemetry.

33. The implantable medical device of claim 32 further comprising non-volatile memory, whereby device status information and patient physiological information is stored and protected when the primary source is depleted for retrieval by the external programmer.

34. The implantable medical device of claim 31 wherein the main power source is a non-rechargeable rechargeable power source.

35. The implantable medical device of claim 31 wherein the main power source is a rechargeable power source.

36. A method for providing an electrical power feed selection for an implantable medical device comprising:
- transmitting radio frequency signals to an antenna of the implantable medical device;
- rectifying the radio frequency signals by a rectifier circuit;
- storing energy contained in the transmitted radio frequency signals in a supplemental power source that comprises an energy storage device;
- comparing voltage levels of an electrical main power source and the supplemental power source and outputting a signal from a comparator indicating which power source is greater;
- receiving a signal from the comparator and selecting the supplemental power source as a power feed when the main power source is depleted; and
- maintaining the voltage level from the supplemental power source at a predetermined level when the supplemental power source has been selected as the power feed, thereby allowing retrieval of patient and device data from the medical device.

37. A method for retrieving information and identification from an implantable medical device with a depleted main power source comprising the steps of:
- activating a supplemental power source within the implantable medical device, the supplemental power source having a power capacity sufficient to immediately energize a controller within the implantable medical device;
- providing power to the supplemental power source from an external programmer via telemetry;
- providing power from the supplemental power source to the controller; and
- retrieving device information and identification from the energized controller via telemetry.

38. An implantable medical device comprising:
- an antenna operable to receive and transmit telemetry signals from the implantable medical device;
- a charging circuit connected to the antenna;
- a main electrical power source connected to a switching mechanism;
- a supplemental power source cooperatively connected to the charging circuit for storing energy transmitted via telemetry signals, said supplemental power source also connected to the switching mechanism;
- whereby the switching mechanism will feed power from the supplemental power source to a controller when the main power source is depleted, thereby reenergizing an inoperative medical device and allowing retrieval of patient and device information from the implantable medical device to the external controller via telemetry.

39. The implantable medical device of claim 38 wherein the switching mechanism is comprised of a comparator and a level shifter.

40. The implantable medical device of claim 39 wherein the comparator is operable to compare the voltage levels of the main power source and the supplemental power source and output a signal indicating which power source has a greater voltage; and the level shifter is operable to receive the output signal from the comparator and permit power to flow from either the main power source or the supplemental power source as a result of the signal received from the comparator to power the controller when the main power source is depleted.

41. An implantable medical device comprising:
a first antenna for receiving and transmitting telemetry signals;
a second antenna for receiving the telemetry signals;
a rectifier circuit connected to said second antenna;
a main electrical power source to supply power to the implantable medical device;
a supplemental power source, connected to the rectifier circuit, comprising an energy storage device for storage of sufficient energy to provide power to energize the implantable medical device, said energy received via telemetry signals from an external source;
a comparator, to compare voltage levels of the main power source and the supplemental power source and output a signal indicating which power source is greater; and
a level shifter operable to receive the output signal from the comparator, whereby the level shifter will permit power to flow from either the main electrical power source or the supplemental power source based on the signal received from the comparator to power the implantable medical device, thereby allowing communication with an external programmer via telemetry retrieval of identification and information of the medical device and the patient.

42. The implantable medical device of claim 41 wherein the supplemental power source further comprises a voltage regulator cooperating with the energy storage device to maintain a voltage level output from the supplemental power source of about 2–5 volts.

43. The implantable medical device of claim 42 wherein the voltage regulator is comprised of zener diodes that maintain the voltage level output from the supplemental power source at a predetermined voltage level.

44. The implantable medical device of claim 42 wherein the energy storage device reaches said sufficient power in a microsecond to millisecond time frame once the telemetry signal is initiated by the external programmer.

45. The implantable medical device of claim 44 wherein the energy storage device can be either a capacitor or a rechargeable battery.

46. The implantable medical device of claim 45 wherein the main power source can be either a rechargeable power source or a non-rechargeable power source.

47. The implantable medical device of claim 46 wherein the telemetry signal is a radio frequency signal.

48. The implantable medical device of claim 47 wherein the implantable medical device can be a pacemaker, a defibrillator, or a drug delivery device.

49. A method for providing an electrical power feed selection for an implantable medical device comprising:
transmitting radio frequency signals to a first and second antenna of the implantable medical device;
rectifying the radio frequency signals received at the second antenna by a rectifier circuit;
storing energy contained in the transmitted radio frequency signals in a supplemental power source that comprises an energy storage device;
comparing voltage levels of an electrical main power source and the supplemental power source and outputting a signal from a comparator indicating which power source is greater;
receiving a signal from the comparator and selecting the supplemental power source as a power feed when the main power source is depleted; and
maintaining the voltage level from the supplemental power source at a predetermined level when the supplemental power source has been selected as the power feed, thereby allowing retrieval of patient and device data from the medical device.

50. An implantable medical device comprising:
a first antenna operable to receive and transmit telemetry signals from the implantable medical device;
a second antenna operable to receive telemetry signals from an external programmer
a charging circuit connected to the second antenna;
a main electrical power source connected to a switching mechanism;
a supplemental power source cooperatively connected to the charging circuit for storing energy transmitted via telemetry signals, said supplemental power source also connected to the switching mechanism;
whereby the switching mechanism will feed power from the supplemental power source to a controller when the main power source is depleted, thereby reenergizing an inoperative medical device and allowing retrieval of patient and device information from the implantable medical device to the external controller via telemetry.

51. The implantable medical device of claim 50 wherein the switching mechanism is comprised of a comparator and a level shifter;
whereby the comparator is operable to compare the voltage levels of the main power source and the supplemental power source and output a signal indicating which power source has a greater voltage; and
the level shifter is operable to receive the output signal from the comparator and permit power to flow from either the main power source or the supplemental power source as a result of the signal received from the comparator to power the controller when the main power source is depleted.

* * * * *

UNITED STATES PATENT AND TRADEMARK OFFICE
CERTIFICATE OF CORRECTION

PATENT NO. : 6,456,883 B1
DATED : September 24, 2002
INVENTOR(S) : Torgerson et al.

It is certified that error appears in the above-identified patent and that said Letters Patent is hereby corrected as shown below:

Column 14,
Line 54, between "device" and "sufficient" insert -- reaches said --.
Line 66, between "be" and "pacemaker" insert -- a --.

Signed and Sealed this

Fifteenth Day of November, 2005

JON W. DUDAS
*Director of the United States Patent and Trademark Office*

UNITED STATES PATENT AND TRADEMARK OFFICE
Certificate

Patent No. 6,456,883 B1                                             Patented: September 24, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Craig L. Schmidt, Eagan, MN (US); Paul M. Skarstad, Plymouth, MN (US); Nathan A. Torgerson, Andover, MN (US); John J. Grevious, Minneapolis, MN (US); Steven L. Jensen, Coon Rapids, MN (US); John W. Forsberg, St. Paul, MN (US); Robert Leinders, Limbricht, Netherlands; and Raymond F. McMullen, Shorewood, MN (US).

Signed and Sealed this Sixteenth Day of May 2006.

ROBERT E. PEZZUTO
*Supervisory Patent Examiner*
Art Unit 3766